United States Patent [19]
Hays et al.

[11] Patent Number: 5,549,381
[45] Date of Patent: Aug. 27, 1996

[54] METHOD AND APPARATUS FOR MIXING POLYMERIC BONE CEMENT COMPONENTS

[76] Inventors: Greta J. Hays, 202 Delta Dr., Marion, Ark. 72364; Michael W. Kleeman, 27 Elm St., Maynard, Mass. 01754; Ronald J. Vish, 77 Bartlet St., Summerville, Mass. 02145

[21] Appl. No.: 445,302

[22] Filed: May 19, 1995

[51] Int. Cl.[6] .................. B01F 13/06; B01F 7/16
[52] U.S. Cl. .................................. 366/139; 366/247
[58] Field of Search .................... 366/139, 245, 366/244, 348, 349, 247, 248, 14; 425/99, 104, 225

[56] References Cited

U.S. PATENT DOCUMENTS

| | | |
|---|---|---|
| 1,030,868 | 7/1912 | Brophy . |
| 1,794,874 | 3/1931 | Trescott . |
| 2,696,022 | 12/1954 | Steinbock et al. ............ 18/30 |
| 2,777,177 | 1/1957 | Steinbock, Jr. et al. ........ 22/35 |
| 2,958,517 | 11/1960 | Harker et al. ............ 259/122 |
| 2,973,187 | 2/1961 | Wehmer ................. 259/108 |
| 3,006,614 | 10/1961 | Beach .................... 259/104 |
| 3,063,813 | 11/1962 | Weinbrenner et al. ........ 23/252 |
| 3,113,169 | 12/1963 | O'Brien ................... 266/22 |
| 3,131,912 | 5/1964 | Steinbock, Jr. ........... 259/108 |
| 3,358,971 | 12/1967 | Steinbock, Jr. ........... 259/107 |
| 3,366,369 | 1/1968 | Ravasi .................... 259/67 |
| 3,521,863 | 7/1970 | Graham ..................... 259/3 |
| 3,610,586 | 10/1971 | Price ..................... 259/15 |
| 3,640,510 | 2/1972 | Lea ..................... 259/108 |
| 3,738,619 | 6/1973 | Shirae .................. 259/108 |
| 3,918,687 | 11/1975 | Hübers et al. ............. 259/4 |
| 4,015,945 | 4/1977 | Frankel . |
| 4,185,072 | 1/1980 | Puderbaugh ............... 422/99 |
| 4,185,078 | 1/1980 | Quatrini . |
| 4,197,646 | 4/1980 | Morrison ................. 433/97 |
| 4,277,184 | 7/1981 | Solomon ................. 366/139 |

(List continued on next page.)

FOREIGN PATENT DOCUMENTS

| | | | |
|---|---|---|---|
| 7612 | 11/1898 | Norway .................. 366/320 |
| WO93/10892 | 6/1993 | WIPO ................... B01F 7/00 |
| WO93/22041 | 11/1993 | WIPO ................... B01F 3/12 |
| WO94/05415 | 3/1994 | WIPO .................. B01F 13/06 |
| WO95/01832 | 1/1995 | WIPO .................. B01F 13/06 |

OTHER PUBLICATIONS

1960 Product Directory, Whip Mix Corporation "Vac–U–Vestor".

Concise Cementing System Brochure (Richards Medical Co.).

L. Chapin et al., "Viscous Mixing In Polymer Reactors", *Industrial Mixing Technology: Chemical and Biological Applications*, vol. 90, pp. 123–129 (1994).

*Primary Examiner*—Robert W. Jenkins
*Attorney, Agent, or Firm*—Pravel, Hewitt, Kimball & Krieger

[57] ABSTRACT

A bone cement mixing apparatus is provided for mixing solid and liquid bone cement components. The apparatus includes a common receptacle base having an interior base surrounded by a continuous side wall with an access opening for accessing the interior. A lid is provided for forming a closure over the top of the receptacle base, the lid having a smaller access opening therethrough. A pair of modular inserts can be selectively placed within the interior of the common receptacle base. The modular components include a mixing bowl and a mixing syringe. Thus, the user can place the bowl or syringe as desired within the receptacle base before mixing bone cement therein. Impellers are provided for each of the mixing vessels including the bowl and the syringe. A vacuum line is provided for sectioning air and gases from the interior of the receptacle base during an addition of liquid or solid bone cement components to either the bowl or the syringe via the smaller access opening in the lid. Because of the smaller size of the access opening in the lid, the vacuum creates a very high velocity air flow that quickly removes noxious odors that are caused by monomers for example such as methyl-methacrylate.

35 Claims, 9 Drawing Sheets

U.S. PATENT DOCUMENTS

| | | | |
|---|---|---|---|
| 4,457,629 | 7/1984 | Liaw et al. | 366/139 |
| 4,463,875 | 8/1984 | Tepic | 222/82 |
| 4,577,973 | 3/1986 | Occelli | 366/139 |
| 4,653,568 | 3/1987 | Baldelli | 164/7.1 |
| 4,671,263 | 6/1987 | Draenert . | |
| 4,721,390 | 1/1988 | Lidgren | 366/139 |
| 4,758,096 | 7/1988 | Gunnarsson | 366/139 |
| 4,787,751 | 11/1988 | Bakels | 366/139 |
| 4,808,184 | 2/1989 | Tepic | 604/56 |
| 4,854,716 | 8/1989 | Ziemann | 366/139 |
| 4,871,261 | 10/1989 | Randklev | 366/139 |
| 4,961,647 | 10/1990 | Coutts et al. | 366/139 |
| 4,966,601 | 10/1990 | Draenert . | |
| 4,973,168 | 11/1990 | Chan | 366/139 |
| 4,994,065 | 2/1991 | Gibbs et al. | 606/92 |
| 5,015,101 | 5/1991 | Draenert | 366/349 |
| 5,051,482 | 9/1991 | Tepic | 525/309 |
| 5,100,241 | 3/1992 | Chan | 366/139 |
| 5,114,240 | 5/1992 | Larsen | 366/129 |
| 5,145,250 | 9/1992 | Planck | 366/139 |
| 5,193,907 | 3/1993 | Faccioli | 366/139 |
| 5,252,301 | 10/1993 | Nilson . | |
| 5,265,956 | 11/1993 | Nelson | 366/139 |
| 5,306,277 | 4/1994 | Bryant | 606/93 |
| 5,328,262 | 7/1994 | Lidgren | 366/139 |
| 5,348,391 | 9/1994 | Murray | 366/139 |
| 5,368,386 | 11/1994 | Murray | 366/244 |
| 5,395,167 | 3/1995 | Murray | 366/139 |
| 5,415,474 | 5/1995 | Nelson et al. | 366/139 |

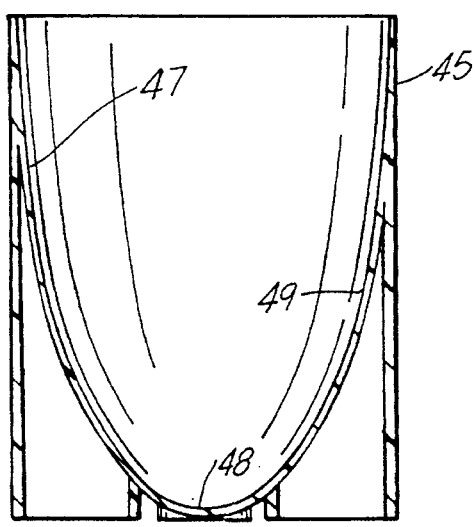
FIG. 8
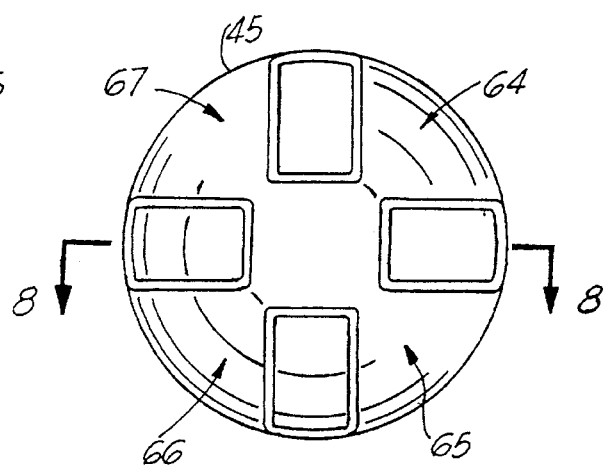
FIG. 9
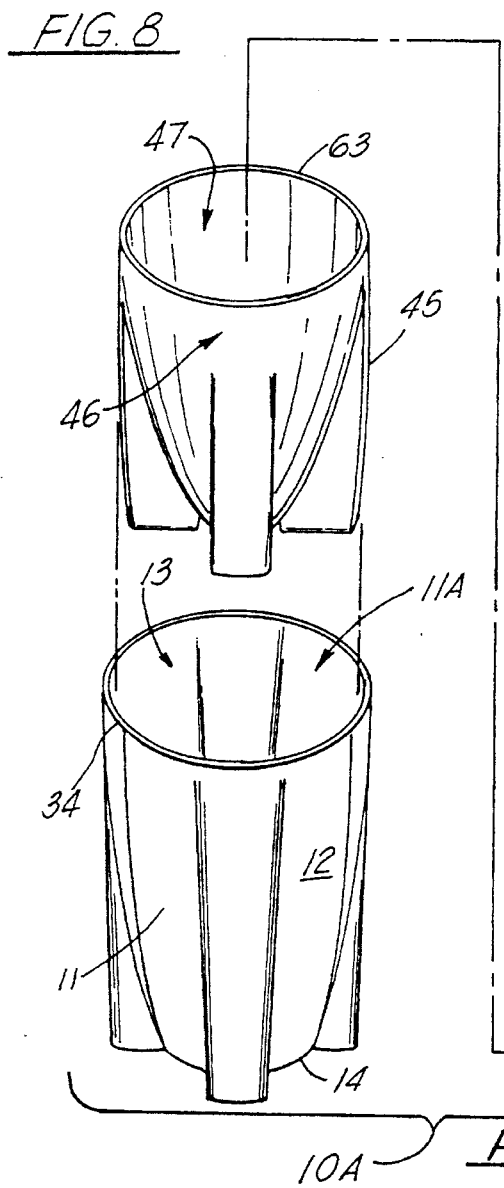
FIG. 7
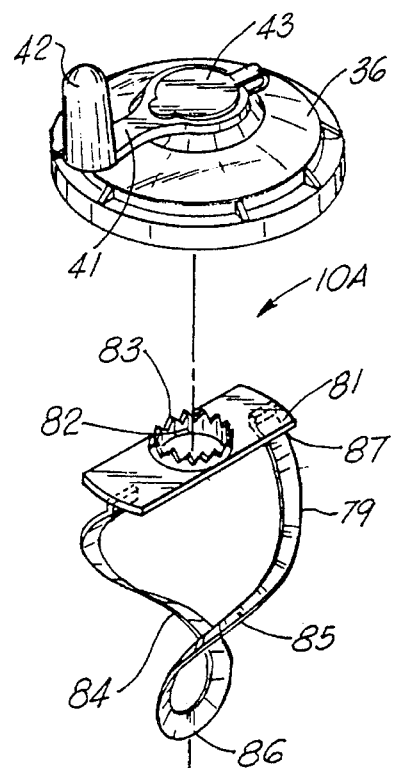

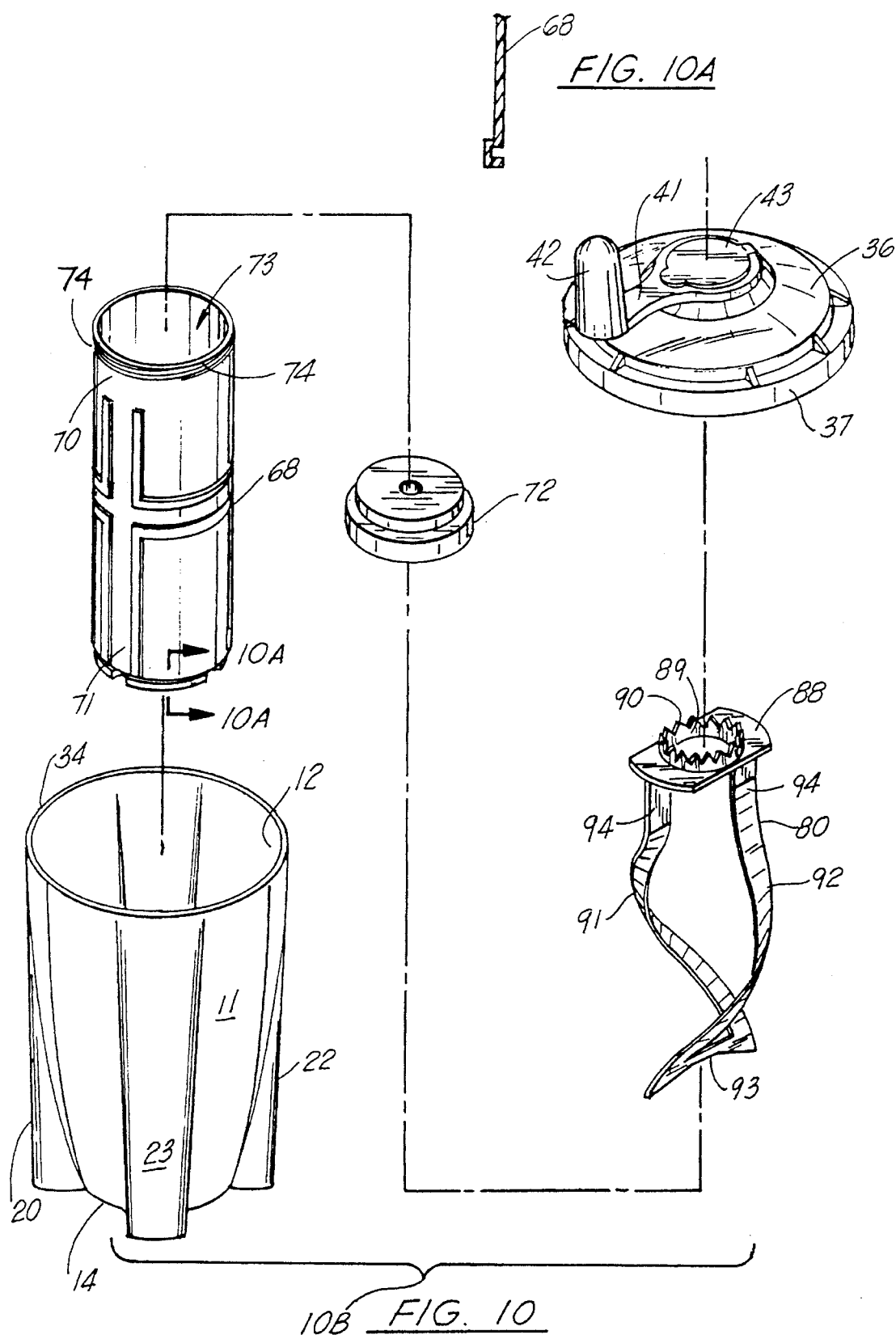

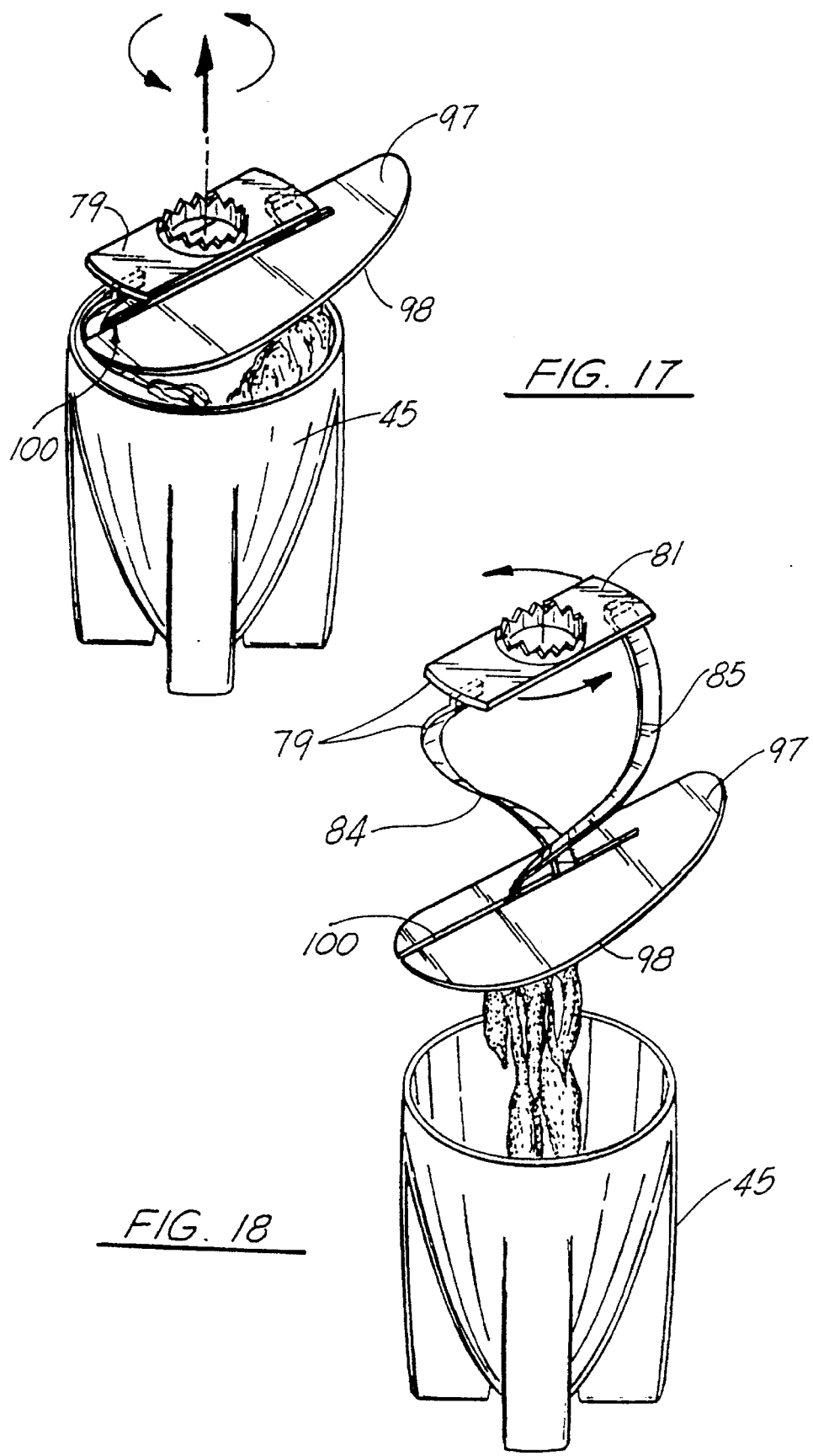

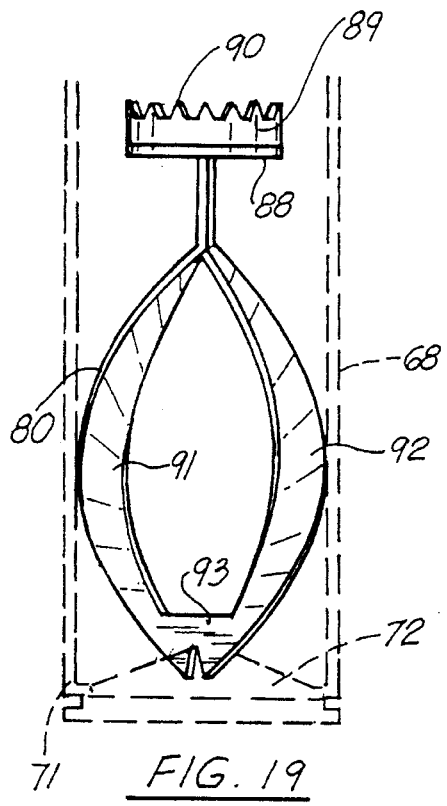
FIG. 19
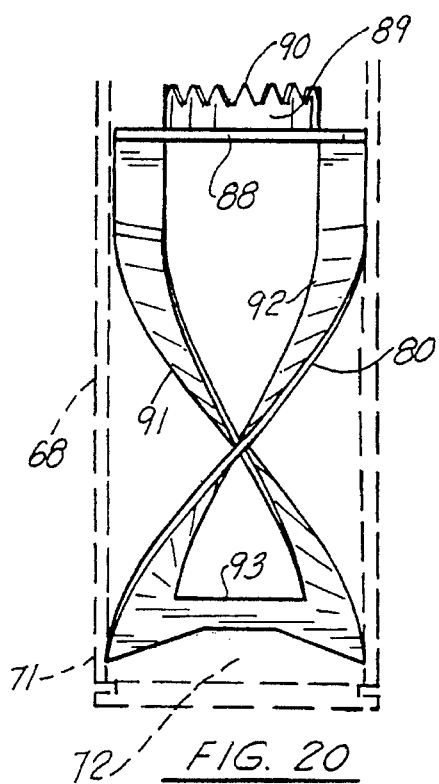
FIG. 20
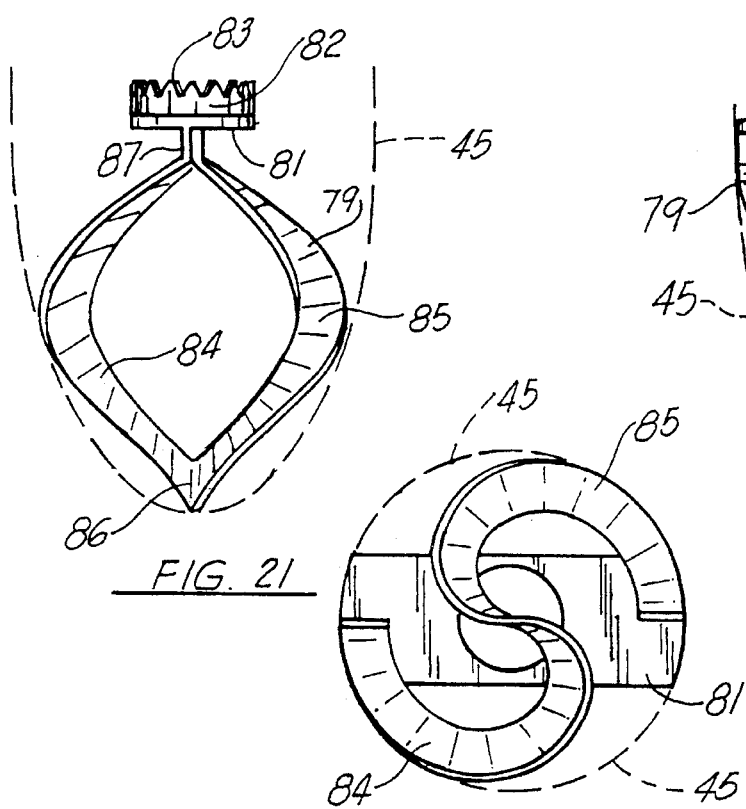
FIG. 21
FIG. 23
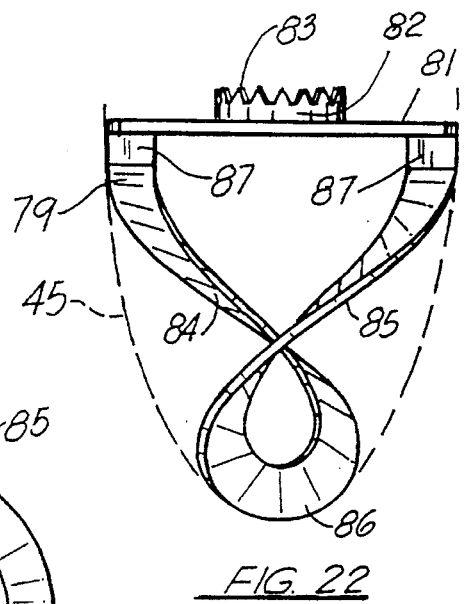
FIG. 22

METHOD AND APPARATUS FOR MIXING POLYMERIC BONE CEMENT COMPONENTS

BACKGROUND OF THE INVENTION:

1. Field of the Invention

The present invention relates to the hand mixing of cement and like compounds that include different components (e.g. a solid component and a liquid component) that mix together and rapidly harden. Even more particularly, the present invention relates to an improved method and apparatus for hand mixing bone cement components wherein a common hollow base receptacle accepts either a mixing bowl or a mixing syringe within an enclosure that is defined by the hollow base receptacle and a lid.

2. General Background

Devices for mixing cement are well known in the art. For many years, various compounds and resins such as bone cement, dental mixtures and the like have been mixed in a container and subjected to a vacuum for removing the air bubbles contained within the cement. The Whip Mix Corporation sold a product in the 1960's known as the "Vac-u-Vestor" that included a vacuum pump for generating a working vacuum in combination with a mixer in a short period of time. Various patents have issued for vacuum mixers that are used to mix cement and the like.

The Frankel U.S. Pat. No. 4,015,945 provides a mixer, for a volatile substance that emits a noxious vapor, that prevents vapors from escaping into the atmosphere. The mixer is made of an outer bowl, open at the top, with an exhaust port in the side. It has a means to connect the exhaust port to a vacuum source. It has a replaceable (disposable) bowl liner, open at the top, that fits into the outer bowl, and spacers that permit fluid flow between the bowl and liner. The liner has several exhaust holes around the open end. The mixer further has a deflector cap that funnels air into the mixer yet permits hand access to the liner for stirring the cement.

The Puderbaugh U.S. Pat. No. 4,185,072 discloses a mixer, for a substance that produces gaseous reaction products, that evacuates the reaction products. The mixer has an outer bowl, open at the top, with an exhaust port in the side that connects to an exhaust means. It has a bowl shaped liner that fits in the outer bowl. Fluid flow is possible between the liner and the outer bowl through at least one vent in the liner, a space between the liner and housing, and the exhaust port. The mixer has a removable top that seals the mixer and keeps gases inside. The top has a mixing paddle acting through it with several open-center arms. At least one of the arms touches the wall of the liner. A crank on the outer side of the top permits rotation of the paddle.

The Solomon U.S. Pat. No. 4,277,184 provides a disposable, plastic, closed-system cement mixer. It consists of a cement cartridge with a barrel and a neck. The piston of the cartridge contains the mixing device. The paddles can move axially out of the piston and they can rotate to mix the cement. The mixer may also include an exhaust port for connection to an external vacuum source.

The Tepic U.S. Pat. No. 4,463,875 discusses a method of preparing and applying bone cement, where the two parts of the cement are vacuum packed in separate, flexible watertight containers. The two containers are abutted along the same axis and mixing takes place when one of the compartments is collapsed into the other. The mixture is then extruded from one chamber to the other several times until mixing is complete. The cement can be extruded by attaching a nozzle in place of one empty chamber.

In U.S. Pat. No. 4,671,263 there is disclosed a bone cement mixing and delivery system with a cylindrical cartridge, a plunger, a cap, a pressurizing unit, and a vent for exhausting the air entrapped in the cement. The system applies pressure to the cement prior to injection and vents the air and gases that separate from the bulk cement.

The Lidren U.S. Pat. No. 4,721,390 discusses a method of mixing bone cement in a mixing space designed to minimize air incorporation. A chilling of the monomer to 2° to 6° C. before mixing is discussed, and applying vacuum before mixing. A mixing of the cement in an operating room where the air and gases are drawn off and exhausted is disclosed by injecting the cement through a syringe and nozzle and injecting the cement under vacuum. The cement is also mixed in the syringe under vacuum.

The Gunnarson U.S. Pat. No. 4,758,096 provides a vacuum cement mixer with an outer vacuum chamber and inner mixing chamber, that connects to an external vacuum source. The mixing chamber has a piston and mixing takes place on top of the piston while vacuum exists on both sides of the piston. The mixer has a hand crank for mixing the cement. The paddle is perforated and scrapes the sides of the mixer.

The Bakels U.S. Pat. No. 4,787,751 provides a bone cement mixer with a cylindrical housing mounted on a plate with a vibrator. A cartridge fits inside the housing to hold the cement. The cartridge is subjected to vacuum and the housing, plate and cylinder are vibrated to mix the cement.

The Tepic U.S. Pat. No. 4,808,184 provides a method of preparing bone cement where the powder is supplied in a partially evacuated chamber and the liquid comes in another chamber. The two containers are joined with an airtight seal and the liquid is pressurized into the powder.

The Ziemann U.S. Pat. No. 4,854,716 provides a cement mixer with a container, a stirrer, a motor for driving the stirrer, a vacuum pump, and a controller for the motor and pump that includes a timer and a buzzer/signal.

The Draenert U.S. Pat. No. 4,966,601 provides a bone cement mixer with a container, a pressurizing device, a vent to release gases from the cement, an evacuating device to exhaust gases, and a means to retain the pressurized cement in the container. The Chan U.S. Pat. No. 4,973,168 provides a cement mixer with a cartridge containing the powder under vacuum, a separate container for the monomer, and a means of passing the monomer into the powder container.

The Draenert U.S. Pat. No. 5,015,101 provides a bone cement mixer with a cylindrical outer container and a cylindrical cartridge fitted with a flange that seals between the cartridge OD and the outer container ID. As the inner cartridge is forced into the outer container, mixed cement extrudes from the outer container into the inner cartridge. A mixing method is disclosed where the cement components are repeatedly pushed from one container to another.

The Tepic U.S. Pat. No. 5,051,482 provides a method of mixing bone cement where the powder is completely evacuated, then flooded with monomer. Excess monomer is drained off. Specific powder morphologies and formulations are disclosed.

The Chan U.S. Pat. No. 5,100,241 provides a cement mixing device where the powder is in an evacuated cartridge. The liquid monomer is introduced into the cartridge through a sealable connection.

The Kindt-Larsen U.S. Pat. No. 5,114,240 provides a method of mixing bone cement where the liquid is forced into the interstices between the powder particles.

The Planck U.S. Pat. No. 5,145,250 provides a method of producing bone cement in a device consisting of a sterile cartridge, stirrer, and automatic controller. Data on the type and quantity of cement is encoded on the cartridge. Inserting the cartridge into a holding apparatus allows the data to be read by an automatic controller. The automatic controller charges the cartridge with the correct cement components and mixes them automatically. An automatic resting phase follows. Reduced pressure in the mixing chamber is possible during at least part of the cycle. Further disclosures relate to exhausting gases from the mixer, filtering entering and exhausting air, chilling the cement components, storing cement components in bulk and dispensing them into the cartridge at surgery, monitoring temperatures and adjusting mixing accordingly, and controlling the temperature of the mixing cartridge.

The Faccioli U.S. Pat. No. 5,193,907 provides a method of mixing bone cement where the two components are kept in separate chambers within the same container until needed. The container for the liquid component is opened within one chamber, which is sealed from the atmosphere. Drawing a vacuum in the powder chamber causes the liquid to be sucked into the powder chamber. Agitation of the container causes mixing and compression of the cement extrudes it out of the container.

The Nilson U.S. Pat. No. 5,252,301 provides a bone cement mixer with a mixing cylinder where the bottom can move relative to the lid. The mixer has a perforated stirrer that can move axially in the cylinder, and mixing takes place under vacuum. The mixer also serves as a dispenser through a hollow tube.

The Nelson U.S. Pat. No. 5,265,956 provides a cement mixing chamber, a cartridge that attaches to the mixing chamber, and a passageway between the chamber and the cartridge. The chamber's outlet is initially sealed by the piston for the cartridge and there is a rod that pushes the piston into the cartridge when desired. The piston fits tightly in the mixing chamber outlet and slides easily in the cartridge. The rod is inside a hollow shaft which holds the mixing paddles in the mixing chamber. All points of communication between the mixing chamber and the outside are sealed to prevent air entering the mixing chamber.

SUMMARY OF THE INVENTION

The present invention provides an improved bone cement mixing apparatus that allows the mixing of solid and liquid components in any desired order and with minimal exposure to noxious chemicals such as methyl-methacrylate monomer, and the like.

The present invention provides an improved bone cement mixing apparatus that immediately removes vapors, even during the addition of the liquid monomer to the mixing vessel.

The present invention provides an improved mixing apparatus that enables selective use of a mixing bowl or a mixing syringe in an interchangeable fashion with a common receptacle base.

One of the features of the present invention is the use of a very small opening for adding chemicals to the bone cement mix, an opening that is much smaller than the open top of the receptacle being used. This increases air flow velocity into the receptacle when a vacuum source is fitted to the receptacle base for drawing a vacuum on the base interior.

The present invention thus provides an improved bone cement mixing apparatus for mixing separate components of viscous polymers as they react. The apparatus includes a common receptacle base having an interior base surrounded by a continuous side wall. An access opening is providing for accessing the interior of the receptacle base. A lid is provided for closing the access opening. The lid provides a crank and a closable opening preferably at the center of the crank.

A pair of modular inserts are provided for selectively mixing bone cement therein. One of the modular inserts is a bowl. The second modular insert is a syringe. Mixing impellers are provided for each of the modular inserts.

A vacuum port is provided for attaching a source of suction to the receptacle base for removing air and gases from the interior of the receptacle base during mixing of bone cement with either the selected bowl or syringe.

Each insert (bowl and syringe) have specially fitted impellers or paddles. The impellers are preferably helically shaped for each of the inserts. In the preferred embodiment, the common lid has a crank that can drive and rotate the impeller of the syringe or of the bowl as selected by the user.

A filter can be provided for filtering air and gases that exit the interior of the receptacle through the vacuum line.

In the preferred embodiment, the mixing bowl has a curved, parabolic bottom portion. In the preferred embodiment, the syringe is generally cylindrically shaped, having a cylindrical wall and a hollow interior.

In the preferred embodiment, the lid includes a means for rotating the impeller or paddle, preferably a crank that fits the lid and a transmission for transferring rotational energy between the crank and the impeller.

In the preferred embodiment, the base receptacle and lid form a close connection to define a generally sealed enclosure and the lid and base have an interior that can receive either the mixing bowl or the syringe upon assembly, and the lid provides an access opening for adding bone cement components to either the bowl or syringe after the bowl or syringe has been placed within the base receptacle.

The present invention further provides a spatula for removing mixed bone cement from the bowl. The spatula has a contoured face that closely matches the inner wall and bottom of the bowl. The spatula further includes a slot for enabling fast cleaning of the impeller blades to reduce cement waste.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 7 is an exploded view of the preferred embodiment of the apparatus of the present invention showing use of the bowl mixer portion;

FIG. 8 is a fragmentary sectional elevational view illustrating the bowl portion of the preferred embodiment of the apparatus of the present invention;

FIG. 9 is a bottom view of the bowl portion of FIG. 8;

FIG. 10 is a exploded perspective view of the preferred embodiment of the apparatus of the present invention showing use of the syringe mixer portion thereof;

FIG. 10A is a sectional view taken along lines 10A—10A of FIG. 10;

FIG. 17 is a perspective fragmentary view illustrating a removal of a mixing blade from the mixing bowl portion of the preferred embodiment of the apparatus of the present invention;

FIG. 18 is another perspective fragmentary view illustrating a removal of the mixing blade from the bowl portion of the preferred embodiment of the apparatus of the present invention;

FIGS. 19 and 20 are side elevational views of the syringe mixing blade portion of the preferred embodiment of the apparatus of the present invention;

FIGS. 21 and 22 are side elevational views of the bowl mixing blade portion of the preferred embodiment of the apparatus of the present invention;

FIG. 23 is a bottom fragmentary view illustrating the bowl mixing blade portion of the preferred embodiment of the apparatus of the present invention;

DETAILED DESCRIPTION OF THE PREFERRED EMBODIMENT

Figure 1:
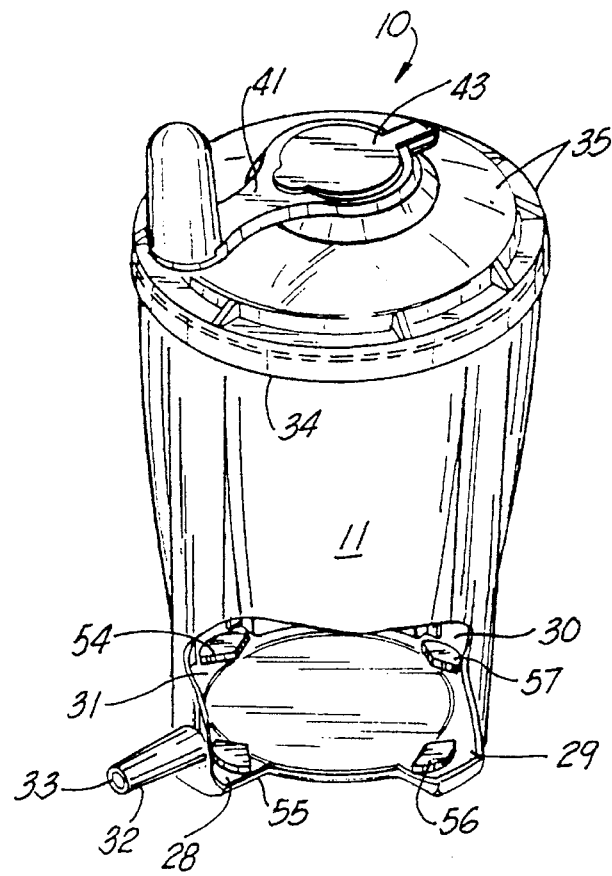
FIG. 1 is a partially cutaway perspective view of the preferred embodiment of the apparatus of the present invention.
Figure 2:
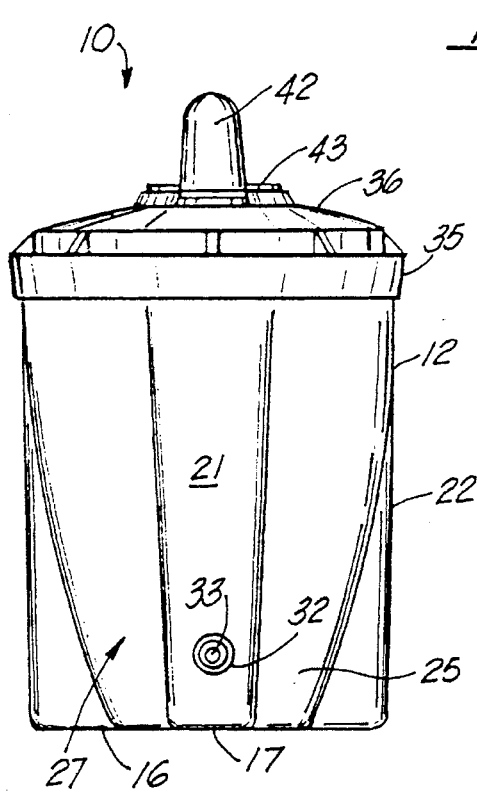
FIG. 2 is a side view of the preferred embodiment of the apparatus of the present invention.
Figure 3:
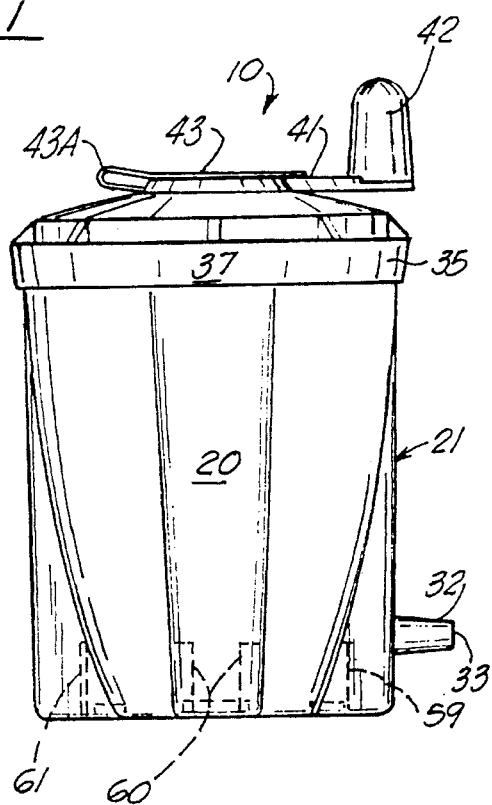
FIG. 3 is another side view of the preferred embodiment of the apparatus of the present invention.
Figure 4:
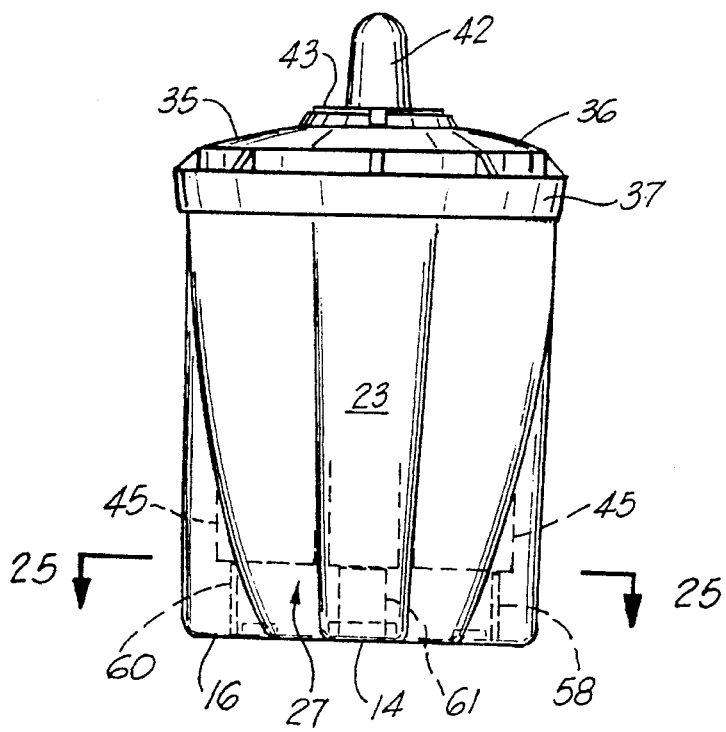
FIG. 4 is an elevational view of the preferred embodiment of the apparatus of the present invention.
Figure 5:
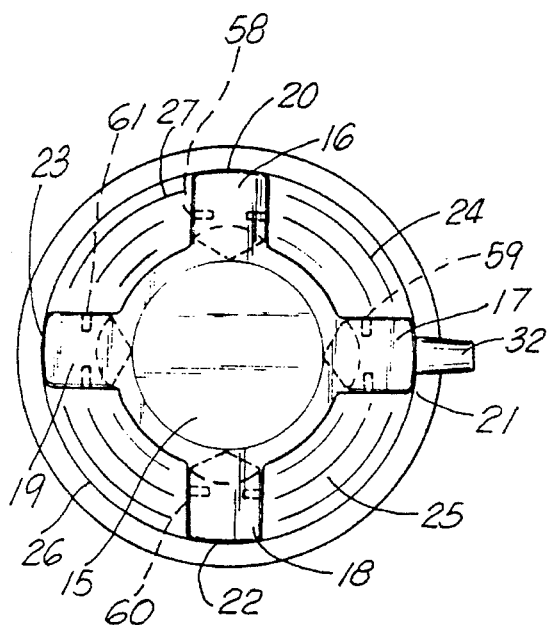
FIG. 5 is a bottom view of the preferred embodiment of the apparatus of the present invention.
Figure 6:
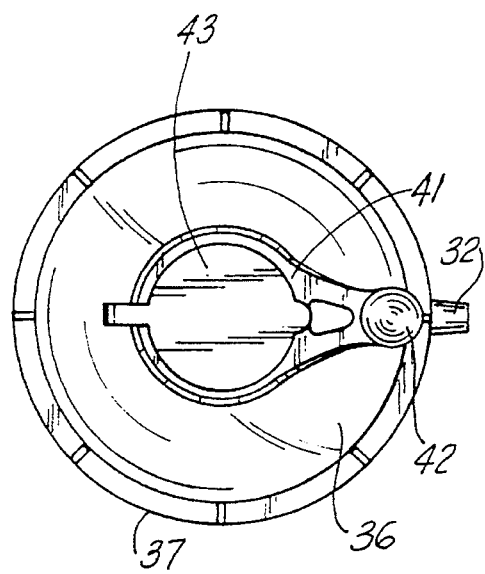
FIG. 6 is a top view of the preferred embodiment of the apparatus of the present invention.

FIGS. 1–14 show generally the preferred embodiment of the apparatus of the present invention designated generally by the numeral 10. In FIG. 7, bone cement mixer 10A designates a selection of mixer 10 with the bowl mixer module. In FIG. 10, bone cement mixer 10B denotes a selection of the syringe mixer module. Bone cement mixer 10 includes a receptacle base 11 that can be used with either of two inserts as will be described more fully hereinafter. The receptacle base 11 provides a side wall 12, open top 13, and closed bottom end portion 14. The bottom end portion 14 includes a generally circular center section 15 and a plurality of rectangular sections 16–19. A plurality of longitudinally extending flat surfaces 20–23 extend from the rectangular sections 16–19 respectively upwardly toward an upper rim 34. A plurality of recesses 24–27 extend longitudinally and are positioned respectively in between longitudinally extending flat surfaces 20–23.

The receptacle base 11 has a hollow interior 11A. At the rectangular sections 16–19 and the longitudinal flat surfaces 20–23, there are provided correspondingly shaped elongated internal sockets 28–31 that communicate with the interior 11A of receptacle base 11. These sockets 28–31 receive projecting portions on the outer surface of a mixing bowl 45. Receptacle base 11 has a tubular fitting 32 with a hollow generally cylindrical shaped bore 33. The fitting 32 allows a source of suction to be attached to the receptacle base 11 at tubular fitting 32 for withdrawing air and gases through the bore 33 during use.

Figure 11:
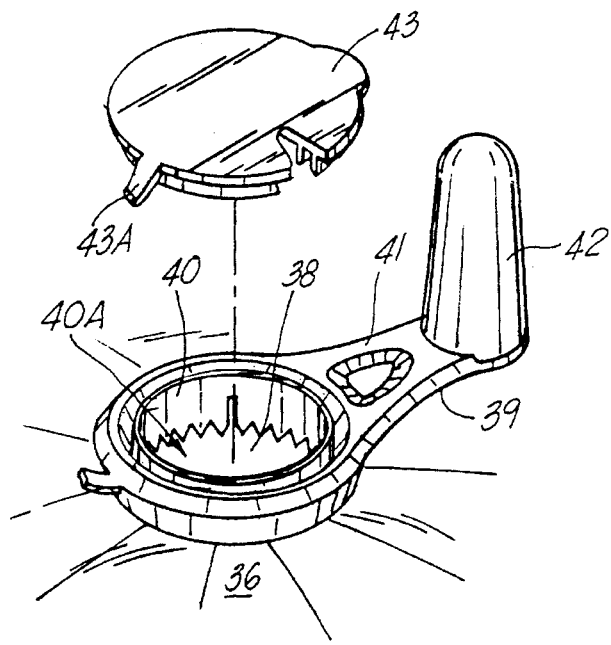
FIG. 11 is a fragmentary perspective view of the preferred embodiment of the apparatus of the present invention.
Figure 12:
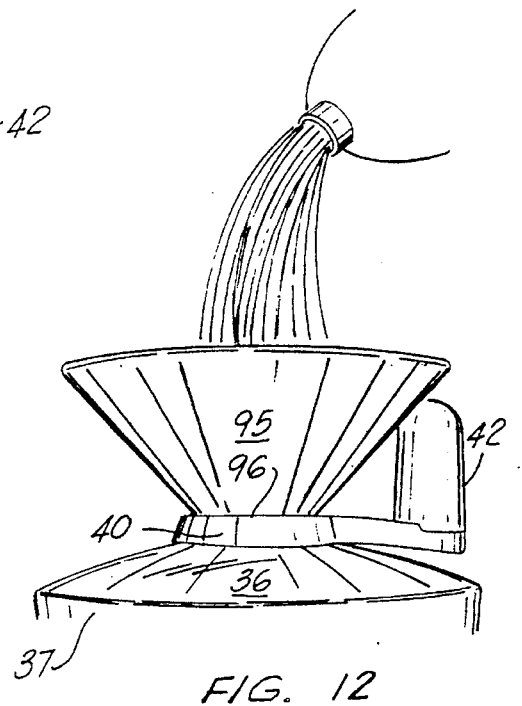
FIG. 12 is another perspective fragmentary view of the preferred embodiment of the apparatus of the present invention shown during a filling of the apparatus with a bone cement component.
Figure 13:
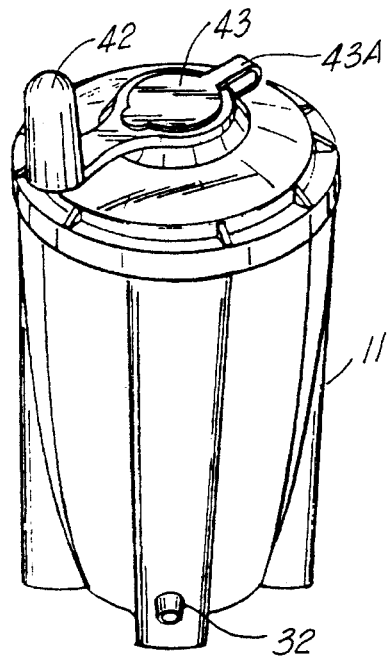
FIG. 13 is a perspective view of the preferred embodiment of the present invention.
Figure 14:
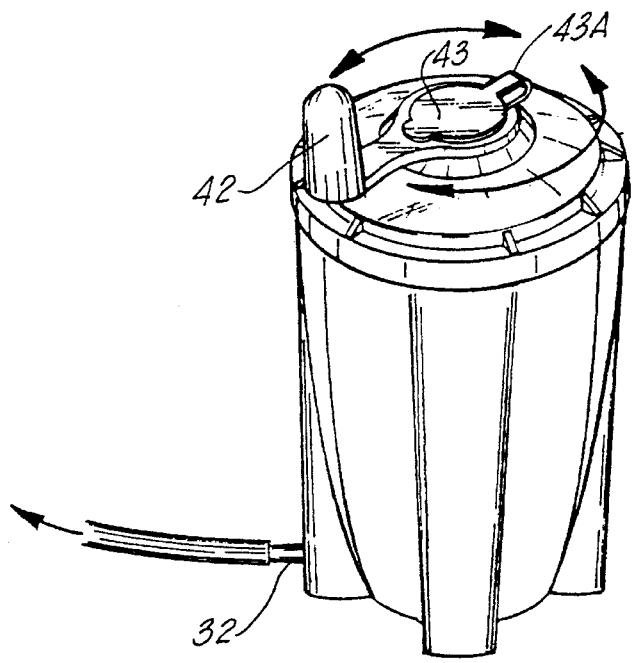
FIG. 14 is another perspective view of the preferred embodiment of the apparatus of the present invention shown during a mixing of bone cement components and with the use of a vacuum source to draw a vacuum on the apparatus interior.
Figure 15:
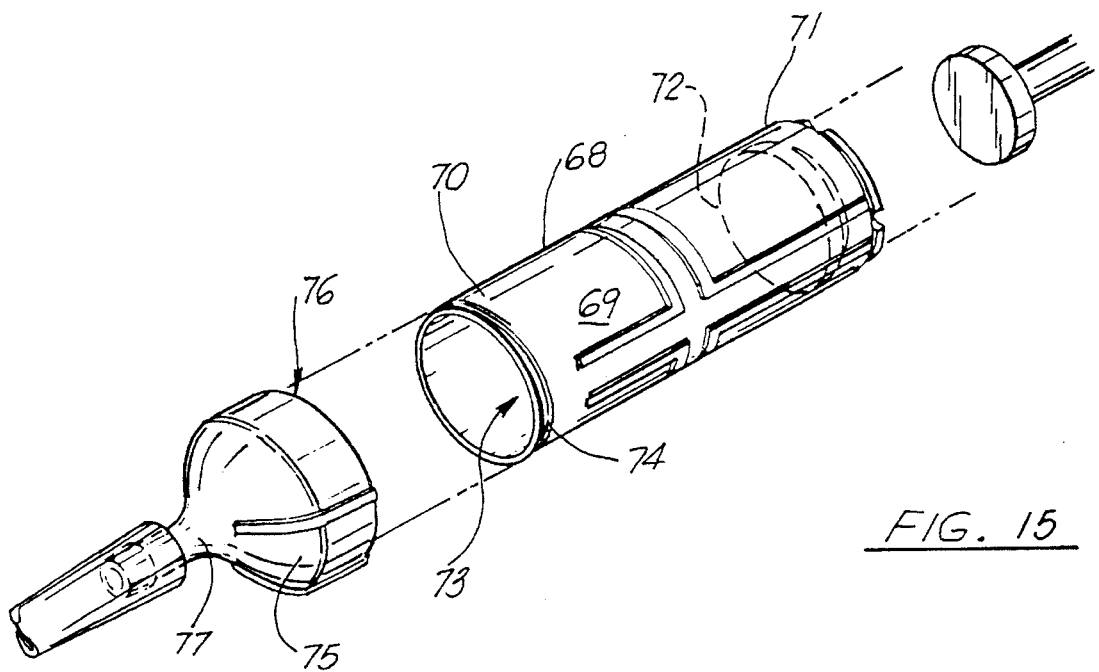
FIG. 15 is a fragmentary perspective exploded view illustrating the syringe portion of the preferred embodiment of the apparatus of the present invention.

Lid 35 fits upper end 34 of receptacle base 11, forming a closure therewith for closing the interior 11A of receptacle base 11. Lid 35 is preferably in the form of a domed member 36 that connects to annular shoulder 37. At the center of concave convex member 36, there is provided a circular opening 38 (FIG. 11). Circular opening 38 receives rotating cylindrically shaped bushing 40 with crank 39 attached thereto.

Figure 26:
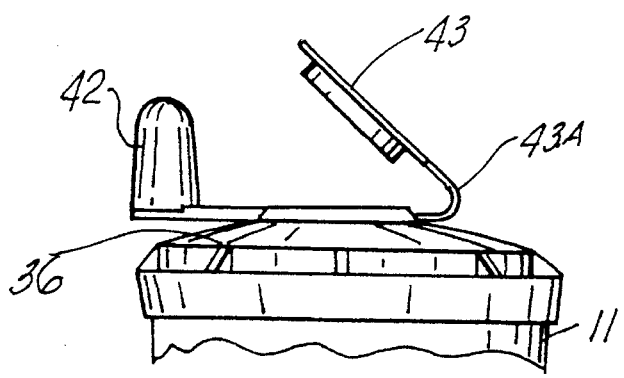
FIG. 26 is a fragmentary elevational view of the preferred embodiment of the apparatus of the present invention.

Crank 39 includes a radially extending arm 41 with knob 42 attached to the free end of arm 41, generally opposite bushing 40 as shown in FIG. 11. During use, the user rotates the crank 39 by holding knob 42 and rotating arm 41 about the circular opening 38. Because bushing 40 is cylindrically shaped, it provides no obstruction to circular opening 38 other than at the periphery of circular opening 38 as shown. Closure cap 43 forms a closure with opening 38 by fitting to the open center 40A of bushing 40. Cap 43 provides an annular shoulder 44 that registers with bushing 40 at open center 40A. Cap 43 can fit an annular seal member on bushing 40 to perfect a seal between cap 43 and bushing. Cap 43 can be joined to bushing 40 with hinge 43A (see FIG. 26).

The user can select either of two mixing components for the mixing of cement. In FIG. 7, one of the two components that can be placed within the interior 11A of receptacle base 11 is bowl 45. Bowl 45 has an outer surface 46 and an inner surface 47. The inner surface 47 provides a concave bottom portion 48 and a curved continuous side wall 49.

The outer surface 46 of bowl 45 provides a plurality of projections 50–53 that respectively register with and fit the sockets 28–31 of receptacle base 11. Vertical struts 58–61 (see FIGS. 3–5 and 25) extend from the bottom 14 of base 11 to support the bottom of bowl 43.

Bowl 45 has a curved outer wall 62 and an upper annular circular rim 63. The annular rim 63 fits immediately under circular opening 38 in the lid and the open center 40A of bushing 40. This allows material to be added to the bowl 45 by pouring the material through the open center 40A of bushing 40 when cap 43 has been opened. A plurality of recesses 64–67 are provided on the outer wall 62 of bowl 45 as shown. The recesses 64–67 correspond and conform to the recesses 24–27 of base 11.

A second component that can be added to the interior of receptacle base 11 is syringe cartridge 68 (see FIG. 10). Syringe 68 has a cylindrical wall 69, and includes a top end 70 and bottom end 71. The syringe 68 is hollow, providing an interior 73 that is generally cylindrically shaped. A circular piston 72 is slideably supported within hollow interior 73 of syringe 68. Piston 72 travels between the ends from 71 to 70 of syringe 68 in order to force bone cement from the syringe 68 during use.

The outer surface of the syringe cartridge 68 has a flange at the bottom. The flange has indentations 101 in it which register with the indexing posts 54–57 in the bottom of the housing 11. The combination of the posts 54–57 and indentations 101 thus center the syringe 68 in the housing 11 and prevent it from freely rotating when mixing takes place.

Figure 16:
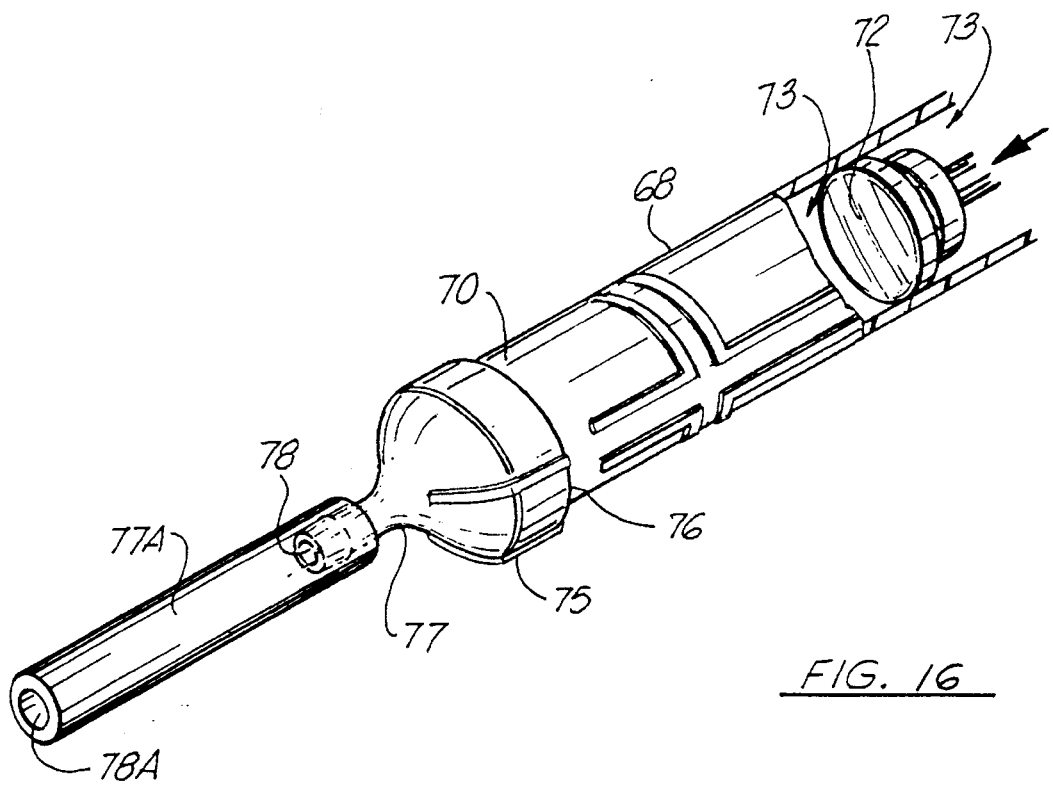
FIG. 16 is a perspective partially cutaway view illustrating the syringe portion of the preferred embodiment of the apparatus of the present invention.
Figure 24:
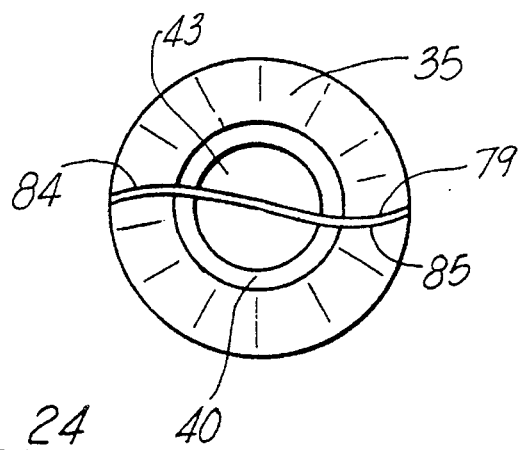
FIG. 24 is a fragmentary transverse sectional view of the preferred embodiment of the apparatus of the present invention showing the configuration of impeller to mixing bowl.
Figure 25:
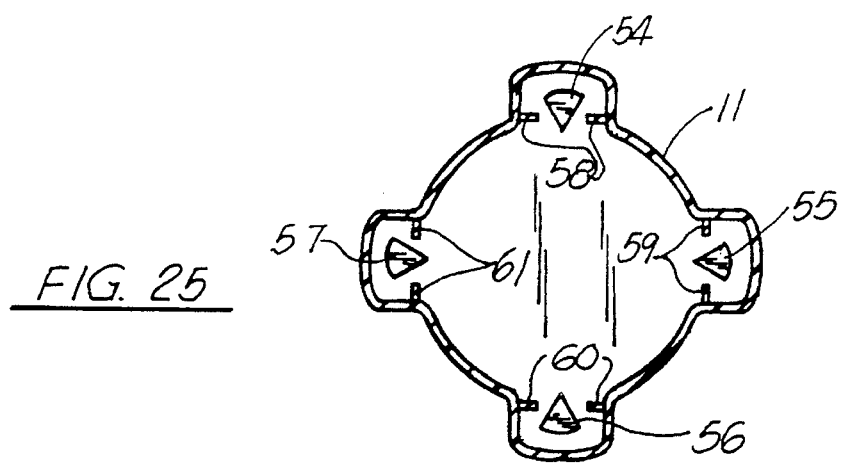
FIG. 25 is a sectional view taken along lines 25—25 of FIG. 4.

Threads 74 form a threaded connection with corresponding internal threads 76 of nozzle section 75. The nozzle section 75 provides a tapered barb fitting 77 end portion having an outlet 78 for discharging bone cement once it has been mixed. One of several nozzle extensions (such as extension 77A with outlet 78A) may be fitted over the barb fitting 77 as shown in FIG. 16. Extensions such as 77A adapt the syringe unit for dispensing cement at various sites. The piston 72 is forced to move along the hollow interior 73 of syringe 78 using a commercially available cement gun such as for example the Smith & Nephew Richards CMW Cement Gun, a commercially available hand operable device. Piston 72 can provide an opening at its center that is preliminarily sealed with a rupturable disk 72A. When piston 72 has moved completely to the upper 70 end of syringe 68 and most contained cement is dispensed, a cylindrical pushrod can be used to puncture disk 72A and clean nozzle 77 and extension 78 of most remaining bone cement.

In FIGS. 19–24, an impeller or paddle is provided for stirring bone cement that is contained in either the bowl 45 or the syringe 68. Bowl impeller 79 is sized and shaped to fit within bowl 45. Syringe impeller 80 is sized and shaped to fit within the hollow interior of syringe 68. Bowl impeller 79 provides a transverse support member 81 having an annular shoulder 82 that carries a plurality of teeth 83. A pair of curved, helically shaped vanes 84, 85 extend from support 81 of bowl impeller 79. The vanes 84, 85 are joined at their lower end at joint 86. The vanes 84, 85 also attach to support 81 at joints 87.

Syringe impeller 80 provides a transverse support 88 to which an annular shoulder 89 is attached. The annular shoulder 89 provides a plurality of teeth 90 and a pair of vanes 91, 92. The vanes 91, 92 join at their lower ends at transverse member 93. The vanes 91, 92 are attached to transverse support 88 as shown in FIGS. 17, 19.

A funnel 95 can be used to add the components of a bone cement mix to either of the selected bowl 45 or syringe 68. During use, the funnel 95 registers with the open center 40A of bushing 40. Thus, the lower end of funnel 95 provides a cylindrical spout 96 having an external diameter that fits the internal diameter of open center 40A of bushing 40. The user can add the selected bone cement components in sequence via the funnel 95 and opening 40A to the selected bowl 45 or syringe 68.

As an alternate mixing method, the user can open the lid and place one of the components of the bone cement mixture within either the bowl 45 or the syringe 68 as selected by the user and then assemble the lid to the device with the selected bowl 45 or syringe 68 within the receptacle base 11. Thereafter, the user can then add the second component via the funnel 95 and cylindrical spout 96.

One of the components of bone cement is often a solid component, such a powder. The user could place the solid (e.g., powder) component within either the bowl 45 or syringe 68 and then close the device 10 by placing either the bowl 45 or syringe 68 within receptacle base 11, covering and closing the interior 11A of the receptacle base 11 by placing the lid 35 over the upper rim 34 of the receptacle base 11. This forms a closure to the interior 11A. The user can add the powder to the bowl 45 or syringe 68 through the open center 40A of bushing 40 after removal of cap 43. The user can place a funnel (see FIG. 12) in open center 40A. The user could simply remove entire domed lid 35 when adding solid or powder to bowl 45 or syringe 68. Other dry ingredients (e.g., antibiotics) can be added in this fashion to the bone cement mix. Examples of antibiotics that can be added in this manner include tobramycin, gentamicin, cefuzanam sodium, amino glycosides, penicillin, and fucidic acid.

The user can remove the cap 43 from lid 35 leaving a small opening to provide access to the interior of the selected bowl 45 or syringe 68. Using a vacuum source attached to tubular fitting 32, the user then creates a vacuum which draws air into the interior 11A of receptacle base 11 and through the open center 40A of bushing 40. The cap 43 is preferably domed. This enables the cap 43 to indicate when sufficient vacuuum has been achieved. The cap 43 is simply shaped in a concave convex domed shape and flattens when a desired vacuum level is obtained. When the cap 43 flattens, the user knows that sufficient vacuum exists. Because the open center 40A is much smaller than the open top 13 of receptacle 11, air flow in the vicinity of the opening 40A will be of increased velocity. This is desirable because the second component added to the bone cement mix is often a chemical having an undesirable odor such as for example methylmethacrylate. Thus, the fumes that are emitted by the methyl-methacrylate are quickly pulled into the interior 11A of receptacle base 11 and discharged from interior 11A through the bore 33 of tubular fitting 32. Such odors can be filtered or collected as desired.

A spatula 97 is provided for removing completely mixed bone cement B from bowl 45. The spatula thus provides a curved edge 98 that corresponds in shape to the curved wall and bottom of bowl 45. The spatula 97 also provides a straight edge 99 that corresponds in shape to the cylindrically shaped side wall of syringe 68. Thus the spatula can be used to remove the remnants of bone cement B from either the bowl 45 or the syringe 68. Spatula 97 also includes a longitudinal slot 100 that is generally parallel to the straight edge 99. The longitudinal slot 100 has a width that corresponds to the thickness of vanes 84, 85 and 91, 92. As shown in the drawings at FIGS. 16–17, the slot 100 can be used to remove the remnants of bone cement from the vanes 84, 85 or 91, 92 after mixing is completed.

Thus, the present invention provides an improved bone cement mixing system that allows the user to add bone cement components in either batch form, or sequentially through the open center 40A of bushing 40 using a funnel as described. Because the components can emit undesirable odors, the present invention provides a small opening for adding certain components to the mix and at the same time provides a vacuum for removing those undesirable odors through the vacuum system. Thus the present invention allows the addition of bone cement components that are solid or liquid. The present invention also allows the addition of bone cement components such as powders including for example antibiotic powders. The present invention allows solid and liquid components to be added in any order without the fear of noxious smells being discharged into the operating room. With the present invention, as soon as the liquid component such a methyl-methacrylate is added the vacuum system immediately removes the vapor. This is important because certain liquid components such as methyl-methacrylate provide low vapor pressure, a very pungent smell, and the smell is evident at very low concentrations of the gas. Further, some research as indicated that certain liquid components of methyl-methacrylate can aggravate asthma possible cause corneal ulcers, produce nausea, and other health problems.

One of the features of the present invention is the enhanced light transmission that allows the user to have a very unobstructed view of the mix during the mixing of components. The lid of the present invention provides an optically clear concave convex, domed construction that is not ribbed. Thus, the user has full 360° visibility of the mix whether the mix occurs in bowl 45 or syringe 68. Further, the present invention preferably utilizes a receptacle base 11 and all other parts of translucent material so that light waves are transmitted on all sides, further enhancing the visibility of the mix during use. This allows visual assurance that mixing is occurring and allows users to assess cement viscosity.

Another feature of the present invention is that the apparatus 10 can be fully assembled in operating position before packaging and shipment to the end user. The apparatus 10 can be shipped as a complete unit either as a mixing bowl version as shown in FIG. 7, or the syringe version as shown in FIG. 10. This provides a method and apparatus for mixing polymeric bone cement components that is ready to be used and is fully operational upon removal from packaging. The apparatus can thus be packaged in a sterilized germ-free container and removed in an operating room environment for immediate use by a surgeon. There is no need for assembly of components in the operating room where time is of the essence and operating room personnel are clothed in surgeon's scrub suits, gloves, hat, and mask.

The following table lists the parts numbers and parts descriptions as used herein and in the drawings attached hereto.

PARTS LIST

| Part Number | Description |
| --- | --- |
| 10 | bone cement mixer |
| 10A | bone cement mixer |
| 10B | bone cement mixer |
| 11 | receptacle base |
| 11A | interior |
| 12 | wall |
| 13 | open top |
| 14 | bottom |
| 15 | circular center section |
| 16 | rectangular section |
| 17 | rectangular section |
| 18 | rectangular section |
| 19 | rectangular section |
| 20 | longitudinal surface |
| 21 | longitudinal surface |
| 22 | longitudinal surface |
| 23 | longitudinal surface |
| 24 | recess |
| 25 | recess |
| 26 | recess |
| 27 | recess |
| 28 | socket |
| 29 | socket |
| 30 | socket |
| 31 | socket |
| 32 | tubular fitting |
| 33 | bore |
| 34 | upper rim |
| 35 | lid |
| 36 | concave convex member |
| 37 | annular shoulder |
| 38 | circular opening |
| 39 | crank |
| 40 | bushing |
| 40A | open center |
| 41 | arm |
| 42 | knob |
| 43 | cap |
| 43A | hinge |
| 44 | annular shoulder |
| 45 | bowl |
| 46 | outer surface |
| 47 | inner surface |
| 48 | concave bottom |
| 49 | curved sidewall |
| 50 | projection |
| 51 | projection |
| 52 | projection |
| 53 | projection |
| 54 | indexing post |
| 55 | indexing post |
| 56 | indexing post |
| 57 | indexing post |
| 58 | vertical strut |
| 59 | vertical strut |
| 60 | vertical strut |
| 61 | vertical strut |
| 62 | curved outer wall |
| 63 | annular rim |
| 64 | recess |
| 65 | recess |
| 66 | recess |
| 67 | recess |
| 68 | syringe |
| 69 | cylindrical wall |
| 70 | top |
| 71 | bottom |
| 72 | piston |
| 72A | disk |
| 73 | hollow interior |
| 74 | threads |
| 75 | nozzle section |
| 76 | internal threads |
| 77 | nozzle |
| 77A | extension |
| 78 | outlet |
| 78A | outlet |
| 79 | bowl impeller |
| 80 | syringe impeller |
| 81 | support |
| 82 | annular shoulder |
| 83 | teeth |
| 84 | vane |
| 85 | vane |
| 86 | joint |
| 87 | joint |
| 88 | support |
| 89 | annular shoulder |
| 90 | teeth |
| 91 | vane |
| 92 | vane |
| 93 | joint |
| 94 | joint |
| 95 | funnel |
| 96 | cylindrical spout |
| 97 | spatula |
| 98 | curved edge |
| 99 | straight edge |
| 100 | longitudinal slot |
| 101 | indentation |
| B | bone cement |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A bone cement mixing apparatus for mixing separate components of viscous polymers as they react, comprising:
   a) a receptacle base having an interior space surrounded by a continuous side wall;
   b) an access opening for accessing the interior;
   c) a lid for closing the access opening, said lid having opening therethrough;
   d) a variety of modular inserts that can be selectively placed within the interior of the receptacle base, said inserts comprising containers for mixing and/or dispensing said polymers;
   e) mixing impeller means having one or more impeller blades that fit the container for mixing bone cement contained within the container; and
   f) vacuum port means for attaching a suction to the receptacle base.

2. The bone cement mixer of claim 1 wherein there are a variety of impeller blades, each contoured to fit a respective insert.

3. The bone cement mixer of claim 1 further comprising means for wiping cement from the impeller blades responsive to removal of the blades through the slits in the spatula.

4. The bone cement mixer of claim 1 wherein the impeller blades are helical in shape.

5. The bone cement mixer of claim 1 wherein the width of the impeller blades is greater than the thickness.

6. The bone cement mixer of claim 1 further comprising filter means disposed at the vacuum port means for filtering gases that exit the interior via the vacuum port means.

7. The bone cement mixer of claim 1 wherein the modular insert is a mixing bowl with a parabolic bottom portion.

8. The bone cement mixer of claim 7 wherein the impeller blade has a parabolic contour portion that tracks the parabolic bottom portion of the insert.

9. The bone cement mixer of claim 1 wherein the modular insert is a syringe that is generally cylindrically shaped, having a cylindrical wall and a hollow, generally cylindrical interior.

10. The bone cement mixer of claim 9 wherein the impeller blade has a generally cylindrically shaped contour portion that tracks the interior of the syringe.

11. The bone cement mixer of claim 1 wherein the lid includes crank means for rotating impeller blade, including a transmission for transferring rotation between the crank means and impeller blade.

12. The bone cement mixer of claim 11 wherein the transmission is releasable from the impeller blade.

13. The bone cement mixer of claim 1 wherein the base receptacle and lid form a connection to define an enclosure, and the said lid and base have an interior that can receive either of the inserts upon assembly.

14. The bone cement mixer of claim 13 wherein the receptacle and lid form a releasable locking connection that secures the lid to the receptacle.

15. The bone cement mixer of claim 13 wherein the opening in the lid has a removable closure cap for sealing the opening.

16. The bone cement mixer of claim 15 further comprises means associated with the lid for indicating to the user that a sufficient vacuum has been obtained during bone cement mixing.

17. The bone cement mixer of claim 16 wherein the indicating means comprises a domed portion of the closure cap that deflects when a sufficient vacuum has been obtained.

18. The bone cement mixer of claim 1 further comprising an opening in the lid for adding either solid or liquid cement components or both to the selected bowl or syringe.

19. The bone cement mixer of claim 1 wherein the vacuum port means enables selective use or non-use of a vacuuum depending upon whether the user is adding a liquid or a powder.

20. The bone cement mixer of claim 1 further comprising a spatula with a slot for cleaning the impeller blades to reduce cement waste.

21. The bone cement mixer of claim 1 wherein the lid is transparent.

22. The bone cement mixer of claim 1 wherein the lid is formed of a uniform thickness concave convex member.

23. The bone cement mixer of claim 1 wherein the receptacle is translucent.

24. The bone cement mixer of claim 1 wherein the modular inserts are translucent.

25. The bone cement mixer of claim 1 wherein the lid provides a 360° optically clear viewing window.

26. A method of mixing bone cement comprising the steps of:
   a) providing a common receptacle having an interior and a pair of modular inserts that each selectively fit the common interior of the receptacle;
   b) placing a selected one of the modular inserts in the interior of the receptacle;
   c) covering the combination of receptacle and insert with a lid that defines an enclosure that can hold a vacuum, the lid having an access opening;
   d) adding bone cement components to the selected modular insert via the opening in the lid; and
   e) mixing the components within the selected insert.

27. The method of claim 26 further comprising the step of subjecting the bone cement components to a vacuum during mixing, 28. The method of claim 26 further comprising the step of subjecting the bone cement components to a vacuum during the adding of components of step "d".

29. The method of claim 26 further comprising the step of subjecting at least some of the bone cement components to a vacuum during the adding of components of step "d".

30. The method of claim 26 wherein the components include a powder and a liquid.

31. The method of claim 30 further comprising the step of indicating when a vacuum has been formed within the receptacle.

32. The method of claim 26 wherein the lid includes a cap.

33. The method of claim 26 further comprising the step of indicating when a vacuum has been formed within the receptacle.

34. The method of claim 32 wherein indication occurs when the cap deflects.

35. The method of claim 26 further comprising the step of indicating on the outside of the assembly of the receptacle and the lid, when a vacuum is formed inside the combination of receptacle and lid.

* * * * *